US005760079A

United States Patent [19]

Shaffer et al.

[11] Patent Number: 5,760,079
[45] Date of Patent: *Jun. 2, 1998

[54] METHOD OF APPLYING ALPHA HYDROXY ACIDS FOR TREATING STRIAE DISTENSAE

[75] Inventors: Burt Shaffer, Huntington, N.Y.; Jeffrey Rapaport, Fort Lee, N.J.

[73] Assignee: Dermatology Home Products Inc., Fort Lee, N.J.

[*] Notice: The term of this patent shall not extend beyond the expiration date of Pat. No. 5,444,091.

[21] Appl. No.: 501,087

[22] PCT Filed: May 23, 1995

[86] PCT No.: PCT/US95/06473

§ 371 Date: Mar. 22, 1996

§ 102(e) Date: Mar. 22, 1996

[87] PCT Pub. No.: WO95/31980

PCT Pub. Date: Nov. 30, 1995

[51] Int. Cl.$^6$ .................................. A61K 35/78
[52] U.S. Cl. ......................................... 514/557
[58] Field of Search ................................ 514/557

[56] References Cited

U.S. PATENT DOCUMENTS

| | | |
|---|---|---|
| 4,054,649 | 10/1977 | Cariel ................... 424/195 |
| 4,105,782 | 8/1978 | Yu et al. ............... 424/283 |
| 4,234,599 | 11/1980 | Van Scott et al. .... 424/279 |
| 4,363,815 | 12/1982 | Yu et al. ............... 424/274 |
| 4,424,234 | 1/1984 | Alderson ............... 424/317 |
| 4,603,146 | 7/1986 | Kligman ................ 514/559 |
| 5,091,171 | 2/1992 | Yu et al. ............... 424/642 |
| 5,134,163 | 7/1992 | Kligman ................ 514/559 |
| 5,153,230 | 10/1992 | Jaffrey ................... 514/847 |
| 5,444,091 | 8/1995 | Rapaport ............... 514/557 |

OTHER PUBLICATIONS

P. Zheng et al. "Anatomy of Striae". British Journal of Dermatology, 112:185–193 (1985).

P. Nigam. "Striae Cutis Distensae". Inter Journal of Dermatology, Sept. 1989 pp.426–428.

Thomas et al. "The Therapeutic Uses of Topical Vitamin A Acid". Journal of the American Academy of Dermatology, 4:505–513 (1981).

Elson et al. Treatment of Striae Distensae with Topical Trentinoin J. Dermatol Surg Oncol 16:3, Mar. 1990, pp.267–269.

Lavker et al. "Effects of Topical Ammonium Lactate on Cutaneous Atrophy from a Potent Topical Corticosteroid", Journal of the American Academy of Dermatology, (1992) pp.535–543.

*Primary Examiner*—Rebecca Cook
*Attorney, Agent, or Firm*—Alfred M. Walker

[57] ABSTRACT

A method is provided to treat and/or prevent striae distensae lesions by topically applying to the skin affected with the lesions an effective amount of a treatment composition containing an alpha hydroxy acid, such as glycolic acid, preferably by daily application in a pharmaceutically acceptable vehicle, such as a cream base, at a concentration of from 2 to 30 percent by weight. When applied during the striae rubrae stage, the alpha hydroxy acid may be effective to prevent the formation of striae albae lesions, and when applied in either stage, the alpha hydroxy acid may be effective to reduce the width and depth of the lesions, and improve the color of striae rubrae.

12 Claims, No Drawings

METHOD OF APPLYING ALPHA HYDROXY ACIDS FOR TREATING STRIAE DISTENSAE

This is a 371 of PCT/US95/06473 filed May 23, 1995.

FIELD OF THE INVENTION

The present invention is directed to a method of treating lesions of striae distensae, more particularly, to a method of preventing striae albae lesions, reducing the size of lesions of both striae albae and striae rubrae, as well as reducing the color of striae rubrae marks.

BACKGROUND OF THE INVENTION

Striae distensae lesions are skin stretch marks, and are most common in women, after puberty or after a first pregnancy. Skin stretch marks originate because of stretching of the skin from weight gain, or mechanical stresses, such as from strenuous exertion, weightlifting and the like. Approximately 50 percent of pregnant women will develop striae distensae skin stretch marks, on the thighs, abdomen and/or breasts. Striae distensae may also be present in cachectic states, such as tuberculosis and typhoid fever, and may be caused by rapid dieting.

Striae distensae stretch marks begin as an inflammation, such as striae rubrae, and progress ultimately to the white stretch marks known as striae albae. The earlier stage striae rubrae are red, elevated, linear lesions. Later they flatten and the redness fades, resulting in a permanent, undulating depressed line, which is the striae albae. Previously, stretch marks were thought to be permanent.

Treatment of striae distensae has been discussed in the prior art. P. Zheng et al., in "Anatomy of Striae", *British Journal of Dermatology*, 112:185–193 (1985), reports that striae albae are scars from an inflammatory process that destroys elastic fibers.

Nigam reports the beneficial treatment of striae distensae with retinoic acid in "Striae Cutis Distensae" *Inter Journal of Dermatology* September 1989 p.426–428.

Retinoic acid has been previously applied topically to the skin for the treatment of many other skin disorders, such as described in Thomas et al., "The Therapeutic Uses of Topical Vitamin A Acid", *Journal of the American Academy of Dermatology*, 4:505–513 (1981), wherein the use of tretinoin is shown to have a beneficial anti-inflammatory action for treating chronic skin dermatoses such as psoriasis and lichen planus.

According to U.S. Pat. No. 4,603,146 to Kligman, topical retinoic acid is shown to be effective to cause the formation of new collagen fibers, generate blood vessels, correct abnormalities in elastic fibers, and eliminate neoplastic growths in chronically sun damaged skin. Retinoic acid is also suggested for treating sun damaged skin as a result of excessive exposure to ultra-violet radiation. U.S. Pat. No. 5,143,163, also to Kligman, describes the treatment of striae distensae skin stretch marks with retinoic acid.

Elson reports treatment of striae distensae with topical tretinoin in Treatment of Striae Distensae with Topical Tretinoin" J. Dermatol Surg Oncol 16:3 March 1990 p.267–269.

Further, U.S. Pat. No. 4,054,649 to Cariel discloses the treatment of skin stretch marks with compositions containing alchemilla used in the form of concentrated hydroglycolic extracts, such as phytelenes, sorbitolisates, oleates, glycerisates, glycolisates, hydroglycolisates, hydroalacoholisates and the like.

Cariel '649 patent is concerned with a composition which contains hydroglycolic extracts, which are very different from an alpha hydroxy acid, such as glycolic acid.

Moreover, extract of Alchemilla, as with other crude natural extracts, may contain 10–100 thousand or more organic compounds, which can only be demonstrated to be present by using the most sophisticated and sensitive chemical detection methods. An end use patent utilizing a dozen well chosen natural crude extracts would therefore cover the great majority of naturally occurring carbon compounds for this end use.

Therefore, while glycolic acid may exist in trace amounts in Alchemilla, this is similar to trace amounts found in any biological organism when properly assayed with a nuclear magnetic resonance (NMR) mass spectrophotometric methodology.

In addition, Cariel '649 claims pharmaceutical activity for the extract of Alchemilla, not the excipients and/or menstrums used to obtain this extract. For instance, at column 2, lines 28–31 therein, there is a list of a number of menstrums and agents to enhance the removal of the active components from the Alchemilla herb. In this context, hydroglycolic extract is clearly used, as shown at lines 35–38, in a generic sense as an extractive agent, i.e. propylene glycol. This term hydroglycolic extract means a plant concentrate extracted or removed from the inert botanical matrix with a mixture of water and a glycol alcohol such as propylene glycol or glycerine. Glycolic acid has very different chemical properties than glycol alcohols, and is not used in the herbal processing industry as an extractive agent. This extraction methodology described is just standard herbal processing industry protocol such as hydroalcoholic and hydroglycolic menstrums, and is therefore not unique. What was described as unique in Cariel '649 is the end use application of Alchemilla extract, which is not related to the subject matter of the above identified patent application for the use of glycolic acid.

Needless to say, the hydroglycolic extract compositions disclosed by Cariel '649 are simply not the compositions defined in the present claims and Cariel '649 does not suggest the use of the glycolic acid as in the composition of the present invention for therapeutic use of skin stretch mark disorders.

Heretofore, various alpha hydroxy acids such as glycolic acid has been used in dermatology for treatment of skin disorders. For example, U.S. Pat. No. 4,105,782 to Van Scott and Yu concerns the treatment of acne and dandruff with an alpha-hydroxy acid or ammonium or organic salts thereof. U.S. Pat. No. 4,105,782 also suggests the same compositions for treating dry skin.

U.S. Pat. No. 4,234,599 to Van Scott and Yu concerns the treatment of skin keratoses with alpha-hydroxy acids, such as glycolic acid and U.S. Pat. No. 4,363,815 to Van Scott and Yu discloses the use of alpha hydroxy acids for treatment of skin irritating or scalp related conditions, such as dry skin, ichthyosis, hyperkeratosis, dandruff, Darier's disease, lichen simplex chronicus, keratoses, acne, psoriasis, eczema, pruritus, warts, and herpes. However, these skin conditions appear to be characterized by increased skin thickness, mostly epidermal or disturbed keratinization. In general, whereas in striae distensae skin stretch marks, the pathological alterations are predominantly dermal, such as collagen alterations and scar formations, and often show a thinning of the epidermal layer.

Further, U.S. Pat. No. 5,091,171, also to Van Scott and Yu, concerns the use of combinations of alpha-hydroxy acids and amphoteric agents for skin disorders, such as wrinkles, and U.S. Pat. No. 4,424,234 to Alderson, deals with the use of particular alpha hydroxy carboxylic acids in aqueous solutions such as lotions, face creams, sunscreen creams, aerosol sprays, hand creams, and skin masks for treating dry skin conditions. Alderson also suggests the use of such compositions to maintain skin suppleness and skin flexibility by temporary skin moisturization.

In addition, U.S. Pat. No. 5,153,230 to Jaffrey, concerns the use of glycolic acid in combination with vitamin A palmitate and vitamin E acetate for treating aging skin.

While Alderson and other prior art disclosures are directed to the use of alpha-hydroxy acids to maintain temporary skin suppleness and temporary skin flexibility, which are related to temporary hydration and moisturization, none of the references disclose or even suggest methods for treating skin structural alterations, such as striae distensae (skin stretch marks), of any type.

BRIEF SUMMARY OF THE INVENTION

According to the present invention, a method is provided for preventing and/or treating striae distensae lesions to reduce their size, by topical application of alpha hydroxy acids, preferably lower alpha hydroxy acids such as glycolic acid to the affected area of the skin. The alpha hydroxy acids or salts thereof are applied in a pharmaceutically acceptable vehicle, such as a lotion, cream or gel base, in a concentration of at least 2 percent, preferably from about 5 to 30 percent by weight, generally by frequent periodic application, such as once or twice daily application.

Tests on humans who have undergone rigorous physical activity, such as weightlifting show that topical application of a pharmaceutically acceptable composition containing from 2 to 30 percent of at least one alpha hydroxy acid or alkali metal or ammonium salts thereof, preferably glycolic acid or salts thereof during earlier striae rubrae stage, the glycolic acid prevents or reduces the formation of striae albae. Tests also show that when such compositions are applied in the later striae albae stage, the scars decrease and the skin stretch marks become less wide and less depressed.

DETAILED DESCRIPTION OF THE PREFERRED EMBODIMENTS

In accordance with the present invention, a method is provided for the prevention and/or treatment of striae distensae lesions and associated dermal presentations which may accompany this skin condition. The method comprises the topical application of suitable compositions containing an alpha hydroxy acid or salt thereof. The topical application to the skin of a patient, may be by manually spreading with the fingers or by use of a suitable applicator such as a cotton swab or applicator pad.

In general, the treatment composition suitable for use in accordance with the invention containing an alpha hydroxy acid or salt thereof may be applied in any dermatologically acceptable vehicle such as a gel, lotion or cream base. Other suitable formulations will be apparent to those skilled in the art.

In the present invention, the method for the prevention and/or treatment of striae distensae lesions and associated dermal presentations is by application of a composition containing the alpha hydroxy acid, preferably glycolic acid, in a concentration of the alpha hydroxy acid or salt thereof of from 2 to about 30 percent by weight of the total composition, and preferably from about 10–20 percent by weight of the composition. In general, the amount of treatment composition to be applied to the skin should be below that which presents any danger of causing birth defects by periodic use, such as teratogenicity, in the case of pregnant patients.

Treatment compositions containing concentrations up to about 30 percent by weight of alpha hydroxy acid or salt thereof will not cause any side effects other than some transitory skin irritations.

Alpha hydroxy acids suitable for use in the treatment compositions of the invention can be any acid or alkaline earth or ammonium salt thereof which will improve the condition of the skin to which it is applied, preferably by frequent periodical application over an extended period of time without undue irritation to the skin or any other side effects. In general, any alpha hydroxy acid having to about 6 carbon atoms or mixture thereof, can be used, including, for example, citric acid, pyruvic acid, lactic acid, and preferably glycolic acid.

The topical preparation described above is formulated in any suitable topical carrier such as a cream, lotion, gel, ointment, etc., which may or may not be emulsified and may contain ingredients to improve, modify, or stabilize the formulation physically or cosmetically. These ingredients may include (in any combination), but are not limited to:

a) a hydroquinone or related substance;

b) a suitable keratolytic agent such as an alpha hydroxy acid, or any derivative of such including, but not limited to, items such as a salt, ester, amide, alcohol, alpha keto acid, beta or gamma hydroxy acid, lactone, polymer, or complex of such;

c) a diluent, vehicle, extender or base such as water, alcohol, propylene glycol, oils, petrolatum, polyhydrics, and the like;

d) a gelling or viscosity modifying system which may include fats, synthetic waxes and oils gums, resins, clays, colloidal gellants or modifiers, and the like;

e) preservatives to inhibit or prevent microbiological contamination;

f) anti-oxidants, vitamins, minerals, botanical or animal extracts to protect the formulation from degradation and extend shelf life to enhance the performance of the product; and, g) anti-oxidants, vitamins, minerals, botanical or animal extracts to protect, prepare, or mediate the action of the product on the dermis, by interaction with the product of the dermis or both.

The treatment compositions used in the practice of the invention are intended to be applied to and remain on the skin, as distinguished from treatment compositions which are applied to the skin and subsequently removed by washing, rinsing, wiping or the like.

Generally, the topical applications are applied periodically such as one or two times per day. Significant clinical improvement may be observed after four to twelve weeks of daily treatment, wherein the size and extent of the stretch marks are substantially reduced, with a relief from redness in color.

For pregnant women, topical applications of treatment compositions including alpha hydroxy acids, preferably glycolic acid, or salts thereof, may be applied in the early red stage of striae rubrae after conception, so that the lesions will decrease in size. Permanent scarring can be largely prevented by beginning the treatment of striae distensae in early pregnancy. The treatment regimen continues several months after birth.

When the topical alpha hydroxy acid treatments of the present invention are not started generally until after the striae albae appears, the resulting scars may be reduced in depth and width. Stretch marks may also be reduced in size for cosmetic benefits.

Suitable alpha hydroxy acid treatment compositions work in reducing striae distensae skin stretch marks by virtue of acids such as glycolic acid eliciting a hyperplastic response in the epidermis and dermis that counters the breakdown of collagen cross linking and/or stimulates the permanent production of interfibrillary material, such as glycoaminoglycans, which promote both rigidity and elasticity.

Compositions that may be applied in accordance with the method of treatment of striae distensae of the present invention are illustrated by the following typical cosmetically acceptable compositions for topical application to human skin.

EXAMPLE

The following illustrates a topically applied skin cream which can be prepared using conventional procedures from the following ingredients with typical ranges of acceptable percentages by weight and typical preferred percentage by weight shown.

| Ingredient | Acceptable % Range | Preferred % Range |
| --- | --- | --- |
| Hydroquinone U.S.P. | 0.0–5.0 | 0.5–4.0 |
| Alpha Hydroxy Acid | 2.0–30.0 | 5.0–20.0 |
| Purified Water | 20.0–95.0 | 50.0–80.0 |
| pH adjusting agent | 0.0–50.0 | 1.0–15.0 |
| gum stabilizer | 0.0–5.0 | 0.5–2.0 |
| glycerin | 0.0–15.0 | 1.0–5.0 |
| chelating agent | 0.0–1.5 | 0.05–1.0 |
| Aloe vera gel | 0.0–90.0 | 2.0–10.0 |
| preservative | 0.0–5.0 | 0.5–1.5 |
| emulsifier | 0.0–50.0 | 3.0–15.0 |
| emollient | 0.0–50.0 | 6.0–20.0 |
| anti-oxidant | 0.0–20.0 | 0.5–5.0 |
| vitamins | 0.0–75.0 | 0.5–10.0 |
| botanical extracts | 0.0–40.0 | 1.0–10.0 |
| minerals | 0.0–40.0 | 0.1–2.0 |
| animal extracts | 0.0–10.0 | 0.1–5.0 |

TEST RESULTS

To study the beneficial results of the treating composition of the present invention, eight patients were treated for regimens of from four to twenty-four weeks. The patients were treated with a composition as described in the claims as follows:

| Ingredient | Range (weight by percentage) |
| --- | --- |
| Purified Water | 35–70 |
| Glycolic Acid | 15–20 |
| Ammonium Hydroxide | 1.5–9.5 |
| Magnesium Aluminum Silicate | 0.5–2.0 |
| Hydroxyethylecellulose | 0.1–2.0 |
| Disodium EDTA | 0.01–1.0 |
| Aloe Vera Gel | 2–10 |
| Methylparaben | 0.01–1.0 |
| Emulsifying Wax NF | 2–15 |
| Capric Caprylic Triglyoeride | 2.5–20 |
| Oleth-10 | 0.1–5 |

-continued

| Ingredient | Range (weight by percentage) |
| --- | --- |
| Squalane | 1–10 |
| Dimethicone | 1–10 |
| Propylparaben | 0.1–1.0 |
| Cetyl Alcohol | 0.1–10 |
| White Wax NF | 1–10 |
| Glyceryl Staerate SE | 2–15 |
| Glyceryl Stearate | 5–15 |
| Imidazolidinyl Urea | 0.1–0.9 |
| Chamomile Extract | 0.1–2 |
| Comfray Extract | 0.01–5 |
| Allantoin | 0.01–5 |

Applicant personally observed and supervised the treatment of eight patients with stretch marks of varying causes, using an alpha hydroxy acid, namely, glycolic acid. In each case, significant lightening of stretch marks were noted. In one case, improvement was noted in two weeks. However, some cases required four to eight weeks to notice results.

Below is a list of patients with documented results, using glycolic acid. The subjects were given an 18% Alpha Hydroxy formulation (Glycolic Acid) cream base. They were instructed to use the cream twice per day to the affected areas.

Side effects were few, including local dermatitis and erythema.

OBSERVATIONS

| List of Patients | Patient Characteristics | Stretch Mark Characteristics |
| --- | --- | --- |
| 1. E. R. | Black Male, 30's | exercise induced stretch marks |
| 2. A. E. | Caucasian Female, 20's | thighs, weight gain and loss stretch marks |
| 3. E. L. | Caucasian Male, 17 years old | Corticosteroid induced |
| 4. H. K. | Caucasian Female, 21 years old | Obesity induced |
| 5. R. S. | Hispanic Male, 22 years old | exercise induced |
| 6. S. A. | Caucasian Female, 30 years old | weight-loss induced |
| 7. L. K. | Caucasian Female | upper thigh and buttocks |
| 8. L. J. | Black Female | upper thigh |

CONCLUSIONS

Alpha hydroxy acids, such as glycolic acid, were effective in reducing stretch marks of varying etiologies.

Patient E. R presented and showed pronounced striated skin stretch marks at both areas below the shoulder and above the arm pits. The stretch marks had significant loss of striations, and were reduced in size and extent.

Patient A. E. presented and showed extensive red and white vertically extending stretch marks on the right front thigh. After frequent treatment, there was a significant reduction in redness as well as fading.

Patient E. L.'s cortico steriod-induced skin stretch marks presented raised red marks in the lower side abdominal area. After treatment, there was significant fading and reduction in extent of the stretch marks.

Patient Heather K. presented and showed extensive, deep red cross hatchings. After treatment, the deep red cross hatchings were about all faded twelve weeks later.

Patient L. K. presented and showed significant red and white diagonal stretch marks on the upper right hip and buttocks area. After treatment, patient L. K. had significant fading of the stretch marks.

Patient L. J. presented and showed upper thigh, lower abdominal stretch marks. After treatment, patient L. J.'s stretch marks were significantly reduced.

OBSERVATIONS—CLINICAL

When initially applied to both red and white stretch marks, the skin remained a normal tone, or a mild erythema developed in the surrounding skin after approximately seven to fourteen days.

The white stretch marks began to develop a faint pink to medium pink erythema themselves.

Some of the red stretch marks turned a purple-pinkish hue, and with continued use, started blending into a mild erythema of the surrounding tissue. It was desirable to increase the amount applied and the frequency in order to achieve erythema.

The white stretch marks took a more prolonged time to treat, and in some circumstances did not completely vanish.

Once the stretch marks were diminished to the desired result, the treatment was stopped, and both the stretch marks and the surrounding skin returned to a more natural skin tone.

The majority of patients with white stretch marks noticed a significant improvement, but not complete fading.

The patients with red stretch marks also noticed a reasonable improvement, however, in these cases the patients developed a more complete fading.

The above test of eight patients were a statistically significant sample, which demonstrated the efficacy of the use of an alpha hydroxy acid, namely, glycolic acid, in treating and reducing striae distensae skin stretch marks.

Other changes to the present invention may be made without departing from the spirit or scope thereof when read in conjunction with the appended claims.

I claim:

1. A method of treating striae distensae lesions in a patient consisting essentially of applying topically to the area of the skin affected with said lesions an effective amount of a treatment composition consisting essentially of an alpha hydroxy acid having up to 6 carbon atoms or salt thereof.

2. The method according to claim 1, wherein said treatment composition is applied periodically to the skin area to be treated, said periodic treatment being applied at least once a day.

3. The method according to claim 1, wherein said treatment composition is applied in a pharmaceutically acceptable vehicle containing a concentration of from 2 to about 30 percent by weight of an alpha hydroxy acid or salt thereof.

4. The method according to claim 1, wherein said treatment composition is applied in a pharmaceutically acceptable vehicle at a concentration of about 5 to 20 percent by weight of an alpha hydroxy acid.

5. The method according to claim 3, wherein said pharmaceutically acceptable vehicle is selected from the group consisting of a cream, lotion or gel base.

6. The method according to claim 1, wherein said alpha hydroxy acid is glycolic acid.

7. The method according to claim 1, wherein said treatment composition consists essentially of a salt of an alpha hydroxy acid.

8. The method according to claim 1, wherein said treatment composition consists essentially of an ammonium salt of an alpha hydroxy acid.

9. A method of preventing the formation of striae distensae skin stretch marks on the abdomen in a patient in need thereof consisting essentially of applying topically to the skin of the abdomen an effective amount of a treatment composition consisting essentially of an alpha hydroxy acid, having up to 6 carbon atoms or a salt thereof in a percentage by weight of from about 2 to 30 percent in a pharmaceutically acceptable vehicle.

10. The method of preventing the formation of striae distensae skin stretch marks on the abdomen according to claim 9, wherein said alpha hydroxy acid is included in said treatment composition in a percentage by weight of from about 5 to 20 percent.

11. The method of preventing the formation of striae distensae stretch marks according to claim 9, wherein said alpha hydroxy acid is glycolic acid.

12. The method of preventing the formation of striae distensae according to claim 9, wherein said treatment composition consists essentially of a salt of glycolic acid.

* * * * *